United States Patent [19]
Jokinen et al.

[11] Patent Number: 6,083,876
[45] Date of Patent: Jul. 4, 2000

[54] EFFECT OF HERBICIDES

[75] Inventors: Kari Jokinen, Helsinki; Jussi Hautala, Turku; Liisa Eronen, Joensuu, all of Finland

[73] Assignee: Cultor Corporation, Helsinki, Finland

[21] Appl. No.: 09/202,343

[22] PCT Filed: Jun. 12, 1997

[86] PCT No.: PCT/FI97/00373

§ 371 Date: Dec. 30, 1998

§ 102(e) Date: Dec. 30, 1998

[87] PCT Pub. No.: WO97/47196

PCT Pub. Date: Dec. 18, 1997

[30] Foreign Application Priority Data

Jun. 14, 1996 [FI] Finland ..................................... 962499

[51] Int. Cl.$^7$ .............................. A01N 37/00; A01N 37/44
[52] U.S. Cl. ............................................................ 504/147
[58] Field of Search ..................................... 504/320, 116, 504/147

[56] References Cited

U.S. PATENT DOCUMENTS

| | | | |
|---|---|---|---|
| 4,032,325 | 6/1977 | Kida et al. .................................... | 71/95 |
| 5,324,709 | 6/1994 | Bunji et al. .............................. | 504/236 |
| 5,491,125 | 2/1996 | Albrecht et al. ......................... | 504/206 |
| 5,922,649 | 7/1999 | Pehu et al. ............................... | 504/320 |

*Primary Examiner*—Jose' G. Dees
*Assistant Examiner*—Alton Pryor
*Attorney, Agent, or Firm*—Nixon & Vanderhye P.C.

[57] ABSTRACT

Betaine improves the effects of herbicides. A combination for controlling weeds including betaine and an herbicides for the weeds is described together with other adjuvants and additives. Methods of controlling weeds by the use of betaine and herbicide are also disclosed.

19 Claims, 7 Drawing Sheets

EFFECT OF HERBICIDES

This application is a 371 of PCT/FI97/00373 filed Jun. 12, 1997.

FIELD OF THE INVENTION

The invention relates to the use of betaine for improving the effect of herbicides. It also relates to a combination of herbicide and betaine, and to a method of controlling weeds by the use of herbicide and betaine.

BACKGROUND OF THE INVENTION

Herbicides have a phytotoxic effect on plants, and so they are used in plant production for controlling weeds or totally inhibiting their growth. Herbicides can be non-selective, which means that they destroy all growth, or selective in part or full, whereby they can be used for inhibiting the growth of weeds of only certain crop plants. Most herbicides used today are selective and they can be applied onto growing crop plants without damaging them. The problem with the use of selective herbicides is that particularly when a weed and a crop plant are of a closely related genus, the weed is usually resistant to herbicides. Further, the selectivity between crop plants and weeds changes with the use of herbicides. The increased use of herbicides has also been observed to make weeds more resistant to herbicides. Insufficient or impaired effect, in turn, has led to a further increase in the amount of herbicides used.

Herbicides are also an environmental problem. They are usually synthetic compounds that have a toxic or harmful effect not only on plants but also on animals. The herbicides used in agriculture decompose in the soil mainly by the effect of micro-organisms. The rate of microbiological decomposition of herbicides varies with the structure of the herbicide and the conditions of decomposition. The rate of decomposition can also depend on the amount of herbicide used in such a way that an increase in the amount slows down the decomposition. The herbicides used in agriculture are also spread to surface water and to other water systems, in which they decompose very slowly causing even more severe damage to the environment.

Despite the drawbacks, the use of herbicides has increased greatly over the years. Because of the environmental and other problems involved, efforts are made to keep the use of herbicides in check and under control through legislation.

The effect of herbicides can be improved by various additives or adjuvants. The best results are achieved with naturally susceptible species, but the effect can sometimes also be extended to resistant species. If the resistance is based, for example, on the thickness of the wax layer and/or weak migration of the herbicide in a plant, an adjuvant added to the mixture may impair the strength of the wax layer e.g. by improving the penetrativeness of herbicide molecules.

Adjuvants, however, are synthetic preparations, and they too are a hazard to the environment. Apart from intensifying the phytotoxic effect of herbicides, adjuvants are also phytotoxic as such. As a result of synergism, the harmful effects on both crop plants and the environment increase.

BRIEF DESCRIPTION OF THE INVENTION

Figure 1A:
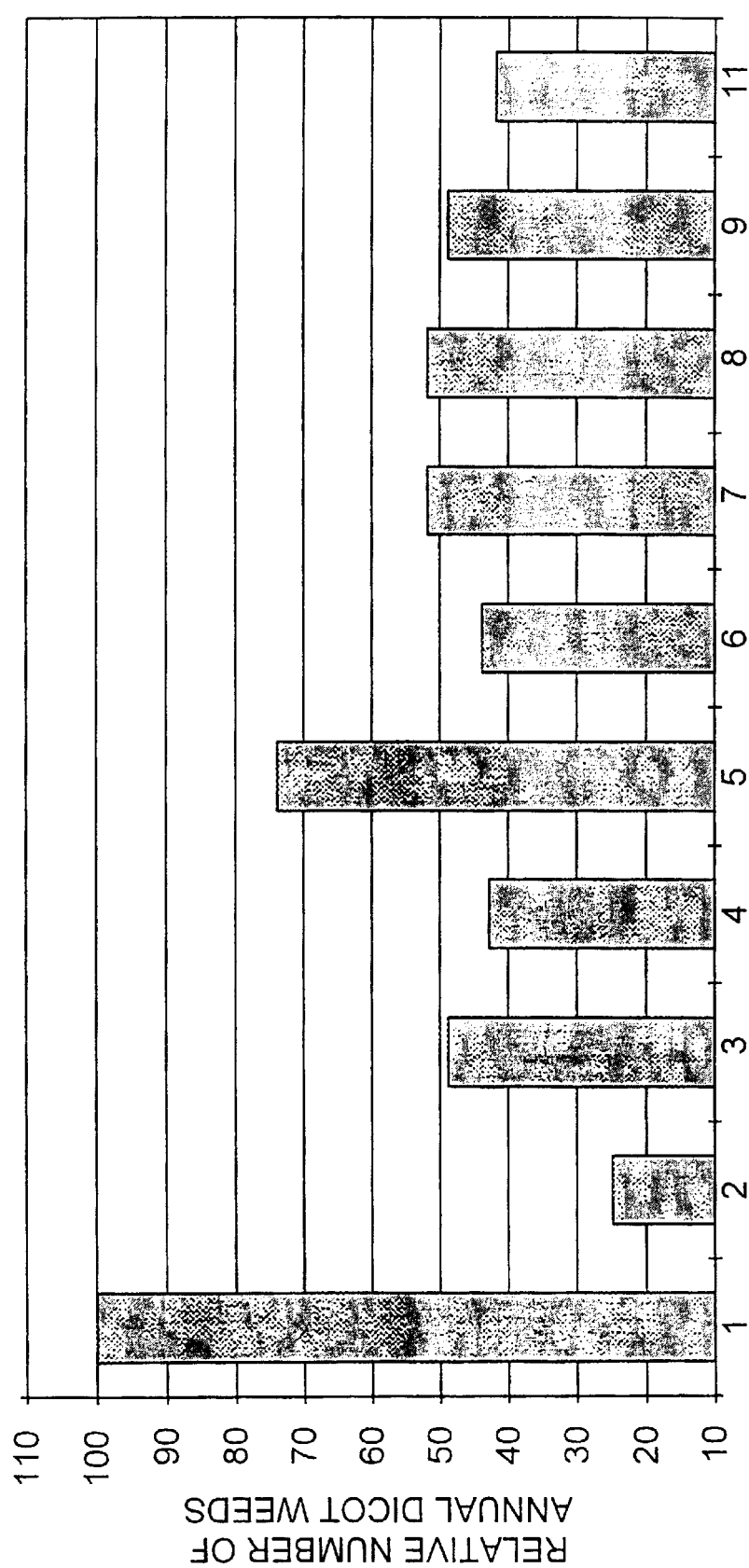
FIG. 1A is a graph showing the summary of results of Example 2 illustrating the effect of betaine and herbicide treatment on the relative number of dicot weeds.

The object of the invention is to find a way of improving the effect of herbicides, simultaneously avoiding the use of substances that are toxic or harmful to plants or animals. Surprisingly, it has been noted that the problem can be solved by the use of betaine. In connection with the current invention, it has been proved that betaine intensifies the effect of herbicides on weeds. Further, betaine is a natural product produced by certain plants, animals and microorganisms, and it has no harmful or toxic effect on plants or animals. To the contrary, betaine has been found to reduce the phytotoxicity of herbicides to crop plants.

The invention thus relates to the use of betaine for improving the effect of herbicides.

The invention also relates to a synergistic composition or combination of betaine and herbicide.

Further, the invention relates to a method of improving the effect of herbicide by the use of betaine.

Still further, the invention relates to a method of controlling weeds by the use of herbicide and betaine.

According to the invention, betaine and herbicide are applied onto plants either at one time or in batches. They can be administered together, or separately but approximately simultaneously. The herbicide and betaine treatment according to the invention is economically advantageous, and the increase in the crop yield is economically profitable and significant, since weed growth can be reduced without adding the amount of herbicide. The treatment does not cause significantly more work, since it may be performed together with other sprayings of fertilisers or pesticides, and it does not require any new investments in machinery, equipment or space. It is also noted that betaine is a non-toxic natural product with no harmful effects on the environment or the quality of the crop. Also, betaine is a stable substance that remains in plant cells and thereby has a long-standing effect.

DETAILED DESCRIPTION OF THE INVENTION

Betaines are fully N-methylated amino acids. Betaines are natural products that have an important function in both plant and animal metabolism. One of the most common betaines is a glycine derivative in which three methyl groups are bonded to the nitrogen atom of the glycine molecule.

This betaine compound is usually called betaine, glycine-betaine or trimethylglycine, and it has the following structural formula:

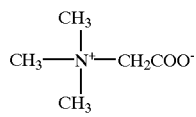

Other betaines include, for example, alaninebetaine, prolinebetaine and histidinebetaine. A detailed description of betaines is given by R. G. Wyn Jones and R. Storey in *The Physiology and Biochemistry of Drought Resistance in Plants,* ed. L. G. Paleg and D. Aspinall, Academic Press, Sydney, Australia, 1981, which is incorporated herein by reference.

Betaine thus has a bipolar structure and it contains several chemically reactive methyl groups, which it can donate in enzyme-catalysed reactions. Most organisms are able to synthesise small quantities of betaine e.g. for the methyl function, but they are not able to produce and store large quantities of betaine. The best known organisms that accumulate betaine are plants of the genus Chenopodiaceae, such as sugar beet, and some microbes, and marine invertebrates. Probably the main reason for these organisms to store betaine is that betaine functions as an osmolyte and thereby protects the cells from the effects of osmotic stress. Unlike many salts, betaine is well compatible with enzymes, and so the betaine content in the cells and cell organelles can be high without that it impairs metabolism. Betaine has also been observed to stabilise the operation of macromolecules in cell membranes: it improves the heat, ion and drought resistance.

At cell level, betaine has been observed to have a plant-protecting effect particularly under stress conditions. The literature of the field contains reports, for example, on the use of betaine as a substance prolonging the shelf life of plants and improving the freeze and drought resistance of growing plants. To enhance growth, betaine has also been added to fertilisers. For example, Japanese patent application JP 63-31800, Laid-open No. 1-208386, is directed to a growth-enhancing fertiliser to which betaine has been added. Fertilisers mentioned in the JP application include common mixtures of inorganic substances, containing, for example, urea, calcium superphosphate, ammonium phosphate, potassium sulphate, potassium nitrate, magnesium sulphate and/or ammonium sulphate, to which betaine is added. According to the publication, the fertiliser can be used for improving a seed germination rate and intensifying plant growth, which improves the yield and shortens the period of growth. Herbicides are not mentioned or described in the publication, and neither is the effect of betaine on the effect of herbicides.

Animals are usually unable to accumulate large quantities of betaine in their cells. It has been observed, however, that when betaine is used as an additive in animal feed or fodder, a similar osmolytically protecting effect is achieved as in plants. The use of betaine as an additive in animal feed also significantly improves animal performance. For example, it has been observed that betaine enhances bowel movement, and adds to feed intake and animal growth. Betaine has also been observed to lower the body fat, for example, in fish, chicken and pig. Further, betaine has been reported to have pharmacological effects. For example, prolinebetaine has been reported to inhibit osteomalacia in chicken, and glycinebetaine has been reported to inhibit harmful effects of coccidiosis in broiler.

Betaine can be obtained, for example, from sugar beet by chromatographic methods. Betaine is commercially available from Cultor Oy, Finnsugar Bioproducts, as a crystalline anhydrous betaine product. Other betaine products, such as betainemonohydrate, betainehydrochloride and betaine-containing raw solutions, are also commercially available and can be used in the way described in the current invention.

In the invention, betaine is thus used with herbicides to improve their effect. Preferred betaines are glycine betaine and its analogues, i.e. betaines having a relatively small molecule size and derived from natural amino acids, e.g. alanine betaine and proline betaine. The most preferred betaine to be used in accordance with the current invention is glycine betaine.

The combined herbicide and betaine treatment according to the invention is suited both for plants that do not normally store betaine in their cells and for plants that can even normally store betaine in the cells.

In the invention, any compound with a herbicidal effect can be used as a herbicide. Herbicides are divided on the basis of their absorption characteristics into leaf herbicides, which are absorbed into plants mainly through leaves, and soil herbicides, which are absorbed into plants mainly through roots. Further, herbicides can be divided into those which act by contact, i.e. destroy only the parts of a plant that they come into immediate contact with, and those which act internally, i.e. migrate to different parts of plant by internal stream flow. With regard to their chemical structure, herbicides are very different. The first herbicides were inorganic compounds that had a non-selective effect, i.e. they were harmful to all plants. Examples for such herbicides are, for example, copper sulphate and certain borates, such as sodium metaborate and disodium octaborate. Most herbicides used today are organic compounds, such as haloalkane acids, phenoxyalkane acids, aromatic acids, amides, nitriles, anilides, nitrophenols, nitrophenyl ethers, carbamates, phenylurea compounds, heterocyclic nitrogen compounds, e.g. triazines, pyridines, pyridazines and pyrimidines, organoarsenic compounds, organophoshorous compounds, sulphonylurea compounds, or imidazolinones. Herbicides are described, for example, in *Progress in Pesticide Biochemistry and Toxicology,* Vol. 6, *Herbicides,* ed. D. H. Hutson and T. R. Roberts, John Wiley & Sons, 1987, and *Kasvinsuojeluseuran julkaisuja* No. 81, 1990, "Rikkakasvien kemiallinen torjunta, Herbisidit ja niiden k äyttö" by Jaakko Mukula and Jukka Salonen, which are incorporated herein by reference.

Herbicides useful in the invention thus include, but not exclusively, e.g. commonly used heterocyclic nitrogen compounds, such as triazines; other heterocyclic compounds, such as paraquat; organoarsenic compounds; organophosphorous compounds, such as glyphosate and gluphosinate; phenylurea compounds; and sulphonylurea compounds, such as primisulphurone, sulphosulphurone, azimsulphurone and ethoxysulphurone. Within the invention, it has been observed that preferable substances in sugar beet cultivation include triazines, particularly 4-amino-4,5-dihydro-3-methyl-3-methyl-6-phenyl-1,2,4-triazin-5-one, i.e. metamitrone; other heterocyclic nitrogen compounds, such as (+-)-2-ethoxy-2,3-dihydro-3,3-dimethylbenzofuran-5-ylmethanesulphonate, i.e. ethofumesate; carbamoylphenyl-carbamates, such as methyl-3-(3-methylcarbaniloyloxy)carbanilate, i.e. phenmedipham, and ethyl-3-(phenylcarbamoyloxy)carbanilate, i.e. desmedipham; and certain urea compounds substituted by organic groups. Herbicides preferable in rice cultivation include, for example, sulphonylurea compounds, which are also effective herbicides against weeds of cereals, soybean, potato and cotton. Glyphosate, which is a total herbicide, is well-suited for cultivation of cereals, and varieties of maize, soybean and cotton made resistant e.g. by gene transfer technology. Gluphosinate is also preferred because of its high rate of decomposition and low toxicity to animals. In cotton cultivation are preferred pyrithiobacsodium, used after emergence, as well as trifluraline, pendimethaline, diurone, fluomethurone, cycloxydime, setoxydime, and fluazifop-P-butyl. Other preferred herbicides include oxyacetamides, which are effective, for example, in controlling weeds of cereals, soybean, potato and cotton. The most preferable herbicides to be used in accordance with the current invention together with betaine are triazines, glyphosate, and sulphonylurea compounds.

The above examples show that several different herbicides can be used with betaine within the scope of the current invention, irrespective of their chemical structure and absorption mechanism. The herbicide is selected e.g. on the basis of the plant species and growth conditions, and this is part of the know-how of a person skilled in the art.

To improve the effect of herbicide, betaine can be added to the herbicide or herbicide mixture during the use, e.g. by adding betaine to the tank-mix. It is also possible to use a combination of betaine and herbicide, e.g. in the form of a commercially available (ready-for-use) product. Alternatively, herbicide and betaine can be applied onto the object separately but approximately simultaneously. The order of application is then irrelevant: betaine can be added either before or after the herbicide. The improving, positive effect of betaine on herbicides is a dual effect: betaine both improves the killing effect of the herbicides and reduces the phytotoxic effect of the herbicides on the crop plants.

In plant production are usually used herbicidal mixtures that contain various herbicides. Herbicides are usually not for sale as active ingredients but as preparations, or mixtures. Most herbicide preparations are concentrates, which are either liquid or solid and are to be diluted either with water, an aqueous solution, or an organic solvent, such as oil. Solid, ready-for-use herbicide preparations are sold in the form of dust or powder. The most common herbicide products are EC (emulsion concentrate), SC (suspension concentrate) and WG (granule suspendible in water) preparations. The form that betaine is used in depends on the application. For the purposes of the current invention, betaine can be used in different forms. For example, solid betaine can be used as such, formulated with an adjuvant, or used as a combination with a herbicide product. To make betaine spread evenly, a betaine solution, particularly an aqueous solution, is preferred. Another preferred embodiment is a combination of betaine and herbicide either as a ready-for-use product or as a solid composition that can be converted to a suitable form.

The betaine- and herbicide-containing combinations and commercial products according to the invention can be formulated by standard methods.

Suspension concentrates, granules or tablets usually contain about 5 to 80% herbicidal active ingredients. In suspension concentrates, water, oil or a mixture of water and oil is used as a carrier liquid. Adjuvants, such as anionic, cationic, non-ionic or ampholytic surfactants, are used for improving dispersibility, suspension stability, wettability, penetration and translocation, for emulsifying oil in the actual concentrate, and for effecting miscibility and suspension/emulsion stability of the preparation in a ready-for-use dilution. The preparations can also contain other adjuvants, such as carriers and/or deflocculating agents miscible and/or soluble in water, i.e. for example kaolin; lignin compounds; anti-foaming agents; thickening agents, such as cellulose derivatives; anti-freezing agents, such as propyleneglycol; organic solvents, such as kerosene; and colouring agents. In addition, preservatives, such as formaline, can be used, particularly if the preparation contains organic suspending and thickening agents. If necessary, the acidity of the suspension concentrate can be adjusted. In granules and tablets to be suspended, it is possible to use as carriers inert inorganic (e.g. silica, salts) or organic (e.g. cellulose, polyacrylates, urea) compounds for diluting active ingredients or adsorbing liquid substances. In addition to the substances mentioned above, other pesticides or nutrients can also be included in the formulates.

The herbicidal active ingredients of the formulates are preferably ground to a particulate form, i.e. have a particle size of less than 10 $\mu$m, preferably from 1 to 3 $\mu$m. They are ground, for example, dry in an air jet mill, or as a suspension in a bead mill. Suspension concentrates can be formulated, for example, in a reactor by efficient mixing, and granules or tablets can be prepared by previously known methods, for example, by disc granulation, spray drying, fluidized-bed granulation, mixing granulation by a vertical mixer or a paddle mixer, or by extrusion, compacting, centrifugal, jet layer, or spraying/cooling granulation.

If the herbicide is used as a suspension concentrate, the betaine can be mixed with a liquid phase. When suspendible granules or tablets are used, liquid betaine can be absorbed into the carriers and solid betaine can be incorporated directly into the granule/tablet mass. In combinations, betaine can be present as separate granules or be included in the same granules as the herbicidal active ingredients.

To apply herbicide and/or betaine, any method suitable for the purpose can be used. Compounds can be applied to either soil or plants, either separately or together with other plant-protecting substances, pesticides or nutrients, such as anti-fungal agents, and urea or micronutrients. A common way of applying herbicides is spraying, whereby they are applied either to soil or to leaves, stems or roots of the plants. Another commonly used method is to apply herbicides to the leaves or stems of weeds with suitable spreading devices or spray guns. To the soil, the herbicide can be applied e.g. as powder as well as as a spray. After the application, the herbicide is either mixed with soil or allowed to absorb into the ground with rain water. The preferred method of applying betaine and any other substances is to spray them onto the leaves of a plant: a more immediate effect is achieved by this method than by methods directed to roots. Various problems, however, may arise in the method: e.g. low penetration in thick leaves, escape from hydrophobic surfaces, elutriation in rain, rapid drying of the solution, and damage to the leaves. To avoid the problems, it is also worthwhile to consider using other methods for applying the compounds.

Even the time of a treatment according to the invention may vary: the treatment can be performed either before sowing, or before or after the emergence. The suitable time is defined by criteria commonly used in the field, taking notice of e.g. the crop plant, the herbicides used, and the cultivation conditions. The substances are administered to the plants either at one time or in batches. It is considered preferable to administer the substances at one time and to perform the treatment at an early stage of growth. The treatment, however, can be repeated several times, if desired.

Betaine is used in a quantity sufficient for achieving the desired effect, i.e. for making the herbicide more effective.

The amount used naturally varies with the method, time and object. A suitable quantity used with or added to herbicide is thus, for example, about 0.010 to 10 kg/ha plants. The quantity is preferably, for example, about 0.1 to 6 kg/ha, more preferably 0.2 to 4 kg/ha, still more preferably 0.5 to 2 kg/ha, and most preferably about 1 kg/ha. The quantity of betaine can thus vary considerably, and so the quantities given must be understood as being only suggestive. All quantities that operate in the manner described herein thus fall within the scope of the invention.

Although the words 'betaine' and 'herbicide' are used in the current publication and claims, it is to be understood that various betaines and/or herbicides can also be used, if desired, in the current invention. It is also pointed out that 'betaine' is here used as a general term that covers different previously known betaines.

The invention will be described in greater detail by the following examples. The examples are presented only for the purpose of illustrating the invention, and so they should not be regarded as restricting the scope of protection in any way.

EXAMPLE 1

The effect of betaine on the biological effect of sugar beet herbicides was studied under field conditions in two different experimental areas: Kärkkä in Salo and Räpi in Köyliö. The field area was divided into three sections in both places. The first section was not treated with herbicides at all, so it became an untreated control area (treatment 1). In the second section, sugar beets were grown normally, using the 3-stage weed control program commonly used in sugar beet cultivation:

$1^{st}$ stage: 1 kg Goltix (Berner Oy, Helsinki; active ingredient metamitrone); 0.2 l Tramat 50 SC (Hoechst-Schering AgrEvo GmbH, Wolfenbüttel; active ingredient ethofumesate); and 1.5 l/ha Betanal (Kemira Agro Oy, Helsinki; active ingredients phenmedipham and desmedipham).

$2^{nd}$ stage: 1 kg Goltix; 0.3 l Tramat 50 SC, and 1.5 l/ha Betanal.

$3^{rd}$ stage: 0.4 l Tramat 50 SC; and 2.0 l/ha Betanal.

The above control program functioned as a comparative trial (treatment 2). To study the effect of betaine, the third section was treated in the same way as the comparative area, except that in the first and second stages, 2 kg/ha glycinebetaine per stage was added to the herbicide mixture. The experiment including betaine is treatment 3.

In Kärkkä, the sowing was performed on May 5, 1995; in Räpi, on May 10, 1995. The emergence took place on May 28 or 29, 1995, and on May 26, 1995, respectively. The treatments were performed by spraying: in Kärkkä on May 31, 1995, Jun. 14, 1995 and Jun. 29, 1995, and in Räpi on May 27, 1995, Jun. 8, 1995 and Jun. 20, 1995. In Kärkkä the sugar beet variety was Freja (Gaucho-90) and in Räpi, Univers (Gaucho-90).

The number and species of weeds were monitored throughout the period of growth. The total number of weeds appears from Table 1a. Table 1b shows the total number of weeds excluding redroot pigweed.

TABLE 1a

Total number of weeds (per $m^2$) after treatments

| Treatment | Experimental area | |
|---|---|---|
| | Kärkkä | Räpi |
| 1. Control | 147.0 | 1249.3 |
| 2. Comparative | 28.5 | 203.0 |
| 3. Betaine | 28.5 | 126.5 |

TABLE 1b

Total number of weeds (per $m^2$) after treatments, excluding redroot pigweed *Amaranthus retroflexus*

| Treatment | Experimental area | |
|---|---|---|
| | Kärkkä | Räpi |
| 1. Control | 72.8 | 1249.3 |
| 2. Comparative | 12.3 | 203.0 |
| 3. Betaine | 7.3 | 126.5 |

The number of weeds was also estimated visually after every treatment on the scale of 0 to 10 where 0=no weeds and 10=growth totally covered by weeds. The results after the first treatment are shown in Table 2a (date of estimation: June 14 in Kärkkä and June 8 in Räpi), and after the second treatment in Table 2b (date of estimation: June 29 in Kärkkä and June 20 in Räpi).

TABLE 2a

Visual estimation of weeds after first treatment. Scale: 0 to 10

| Treatment | Experimental area | |
|---|---|---|
| | Kärkkä | Räpi |
| 1. Control | 10.0 | 10.0 |
| 2. Comparative | 3.0 | 5.3 |
| 3. Betaine | 2.3 | 4.5 |

TABLE 2b

Visual estimation of weeds after second treatment. Scale: 0 to 10

| Treatment | Experimental area | |
|---|---|---|
| | Kärkkä | Räpi |
| 1. Control | 10.0 | 10.0 |
| 2. Comparative | 5.3 | 6.0 |
| 3. Betaine | 3.4 | 4.8 |

The numbers of different annual weeds after the treatments appear from Table 3a; the relative number of some weeds and the effect of the treatments in percentages are shown in Table 3b. The numbers of annual weeds in each experimental area after the treatments are shown in Tables 4a and 4b.

TABLE 3a

Number of different annual weeds (per m²) after treatments

| | Treatment | | |
|---|---|---|---|
| | 1. | 2. | 3. |
| Redwood pigweed  *Amaranthus retroflexus* | 24.8 | 5.4 | 7.1 |
| Shepherd's purse  *Capsella bursa-pastoris* | 0.7 | 0.9 | 0.2 |
| Goosefoots  *Chenopodium sp.* | 141.1 | 5.3 | 3.8 |
| Teacle mustard  *Erysimum cheiranthoides* | 1.0 | 0.0 | 0.0 |
| Fumitory  *Fumaria officinalis* | 0.1 | 0.0 | 0.0 |
| Bedstraws  *Galium spp.* | 0.1 | 0.0 | 0.0 |
| Hemp nettles  *Galeopsis spp.* | 0.2 | 0.0 | 0.0 |
| Dead nettles  *Lamium spp.* | 3.4 | 1.3 | 0.8 |
| Nipplewort  *Lapsana communis* | 0.3 | 0.2 | 0.0 |
| Scentless mayweed  *Tripleurospermum inodorum* | 6.9 | 2.5 | 1.3 |
| Rayless mayweed  *Matricaria matricarioides* | 6.4 | 0.2 | 0.4 |
| Mayweeds Matricaria &  Tripleurospermum spp. | 13.3 | 2.7 | 1.7 |
| Forget-me-nots  *Myosotis sp.* | 7.0 | 0.1 | 0.0 |
| Knotgrass  *Polygonum aviculare* | 16.7 | 7.5 | 4.3 |
| Other bistorts  Polygonum & Fallopia spp. | 0.8 | 0.4 | 0.3 |
| Common chickweed  *Stellaria media* | 6.4 | 0.0 | 0.0 |
| Pennycress  *Thlaspi arvense* | 0.3 | 0.0 | 0.0 |
| Annual nettle  *Uritica urens* | 58.9 | 14.5 | 7.5 |
| Field pansy  *Viola arvensis* | 9.2 | 0.9 | 1.8 |
| Melilots  *Melilotus spp.* | 0.1 | 0.0 | 0.0 |
| Bur-marigold  *Bidens spp.* | 0.0 | 0.2 | 0.1 |
| Annual meadow-grass  *Poa annua* | 266.2 | 39.6 | 26.8 |

TABLE 3b

Relative number of some annual weeds, and effect of treatments in percentages

| | Treatment | | |
|---|---|---|---|
| | 1. | 2. | 3. |
| Goosefoots Chenopodium spp. | | | |
| Relative number | 100 | 4 | 3 |
| Effect % | 0 | 96 | 97 |
| Dead nettles Lamium spp. | | | |
| Relative number | 100 | 38 | 24 |
| Effect % | 0 | 62 | 76 |
| Nipplewort *Lapsana communis* | | | |
| Relative number | 100 | 67 | 0 |
| Effect % | 0 | 43 | 100 |

TABLE 3b-continued

Relative number of some annual weeds, and effect of treatments in percentages

| | Treatment | | |
|---|---|---|---|
| | 1. | 2. | 3. |
| Mayweeds Matricaria &  Tripleurospermum spp. | | | |
| Relative number | 100 | 20 | 13 |
| Effect % | 0 | 80 | 87 |
| Knotgrass *Polygonum aviculare* | | | |
| Relative number | 100 | 45 | 26 |
| Effect % | 0 | 55 | 74 |
| Other bistorts  Polygonum & Fallopia spp. | | | |
| Relative number | 100 | 50 | 37 |
| Effect % | 0 | 50 | 63 |
| Common chickweed *Stellaria media* | | | |
| Relative number | 100 | 0 | 0 |
| Effect % | 0 | 100 | 100 |
| Annual nettle *Urtica urens* | | | |
| Relative number | 100 | 25 | 13 |
| Effect % | 0 | 75 | 87 |
| Annual meadow-grass *Poa annua* | | | |
| Relative number | 100 | 15 | 10 |
| Effect % | 0 | 85 | 90 |

TABLE 4a

Number of different annual weeds (per m²) after treatments in Kärkkä

| | Treatment | | |
|---|---|---|---|
| | 1. | 2. | 3. |
| Redwood pigweed  *Amaranthus retroflexus* | 74.3 | 16.3 | 21.3 |
| Shepherd's purse  *Capsella bursa-pastoris* | 0.3 | 0.0 | 0.0 |
| Goosefoots  *Chenopodium sp.* | 36.0 | 0.8 | 0.3 |
| Teacle mustard  *Erysimum cheiranthoides* | 0.5 | 0.0 | 0.0 |
| Fumitory  *Fumaria officinalis* | 0.3 | 0.0 | 0.0 |
| Bedstraws  *Galium spp.* | 0.3 | 0.0 | 0.0 |
| Dead nettles  *Lamium spp.* | 9.8 | 3.8 | 2.5 |
| Nipplewort  *Lapsana communis* | 0.8 | 0.5 | 0.0 |
| Scentless mayweed  *Tripleurospermum inodorum* | 8.8 | 5.0 | 2.5 |
| Rayless mayweed  *Matricaria matricarioides* | 3.0 | 0.0 | 0.3 |
| Mayweeds Matricaria &  Tripleurospermum spp. | 11.8 | 5.0 | 2.8 |
| Knotgrass  *Polygonum aviculare* | 0.5 | 1.0 | 0.8 |
| Other bistorts  Polygonum & Fallopia spp. | 1.3 | 1.0 | 0.5 |
| Common chickweed  *Stellaria media* | 8.5 | 0.0 | 0.0 |
| Pennycress  *Thlaspi arvense* | 0.3 | 0.0 | 0.0 |
| Field pansy  *Viola arvensis* | 1.3 | 0.3 | 0.3 |
| Melilots  *Melilotus spp.* | 0.3 | 0.0 | 0.0 |

TABLE 4a-continued

Number of different annual weeds (per m²) affer treatments in Kärkkä

| | Treatment | | |
|---|---|---|---|
| | 1. | 2. | 3. |
| Annual meadow-grass<br>*Poa annua* | 0.3 | 0.0 | 0.0 |

Chenopodium spp: *Chenopodium album*, rubrum, glaucum (one Atriplex sp. in the untreated section)
Other bistorts Polygonum & Fallopia spp: *Polygonum lapathifolium, Fallopia convolvulus*.

TABLE 4b

Number of different annual weeds (per m²) affer treatments in Räpi

| | Treatment | | |
|---|---|---|---|
| | 1. | 2. | 3. |
| Shepherd's purse<br>*Capsella bursa-pastoris* | 0.8 | 2.8 | 0.5 |
| Goosefoots<br>Chenopodium spp. | 233.5 | 15.0 | 10.8 |
| Scentless mayweed<br>*Tripleurospermum inodorum* | 11.0 | 2.3 | 0.8 |
| Mayweeds Matricaria &<br>Tripleurospermum spp. | 11.0 | 2.3 | 0.8 |
| Forget-me-nots<br>Myosotis sp. | 21.0 | 0.3 | 0.0 |
| Knotgrass<br>*Polygonum aviculare* | 49.5 | 21.0 | 12.0 |
| Other bistorts<br>Polygonum & Fallopia spp. | 1.0 | 0.3 | 0.3 |
| Common chickweed<br>*Stellaria media* | 8.8 | 0.0 | 0.0 |
| Pennycress<br>*Thlaspi arvense* | 0.8 | 0.0 | 0.0 |
| Annual nettle<br>*Uritica urens* | 131.8 | 42.8 | 22.0 |
| Annual meadow-grass<br>*Poa annua* | 790.0 | 118.3 | 80.0 |
| Bur-marigold<br>Bidens spp. | 0.0 | 0.5 | 0.3 |

Chenopodim spp.: *Chenopodium album*

Any damage to the sugar beet was also estimated after each treatment on the scale 0 to 10 where 0=no damage and 10=growth fully destroyed. No difference was noted between the comparative treatment and the betaine treatment. The damage observed was estimated on the scale 0 to 2. Betaine did thus not have a phytotoxic effect on crop plants.

The results show that an addition of betaine to a herbicide mixture made the control measures much more effective. The addition of betaine usually improved the effect of the mixture against a large number of different weeds found on a sugar beet field. Betaine particularly effectively improved the effect of herbicides on weeds that are usually difficult to control, such as goosefoots (Chenopodium sp.), mayweeds (Tripleurospermum sp.), knotgrass (*Polygonum aviculare*), and grass. The addition of betaine was not observed to have any harmful effects.

EXAMPLE 2

The effect of betaine on the effect of two small-dose herbicides on the market was studied. The herbicides were Logran 20 WG, Ciba-Geigy, comprising 200 g/kg of triasulphurone as an active ingredient; and Ratio, Ciba-Geigy, comprising 500 g/kg of methyltiphensulphurone and 250 g/kg of methyltribenurone as active ingredients. Both preparations have been registered to be sprayed together with an adhesive agent (Citowet or Sito+). To find out the difference in the effect, the recommended quantity of Logran was halved (0.01 kg/ha); Ratio was used in the smallest quantity recommended (0.007 kg/ha). Betaine was used in a dose of 0.01 kg/ha, 0.5 kg/ha, 0.1 kg/ha and 2 kg/ha. In addition, there was an untreated control area. The treatments are presented in Table Sa. The sprayings were performed with a portable propane-operated van der Weij type patch sprayer using 200 l/ha of water.

TABLE 5

Treatments of barley

| Treatment number | Material applied | dose |
|---|---|---|
| 1 | Untreated | — |
| 2 | LOGRAN 20 WG<br>SITO+ | 0.0200 kg/ha<br>0.2000 l/ha |
| 3 | LOGRAN 20 WG<br>SITO+ | 0.0100 kg/ha<br>0.2000 l/ha |
| 4 | LOGRAN 20 WG<br>SITO+<br>betaine | 0.0100 kg/ha<br>0.2000 l/ha<br>1.0000 kg/ha |
| 5 | LOGRAN 20 WG<br>betaine | 0.0100 kg/ha<br>0.1000 kg/ha |
| 6 | LOGRAN 20 WG<br>betaine | 0.0100 kg/ha<br>0.5000 kg/ha |
| 7 | LOGRAN 20 WG<br>betaine | 0.0100 kg/ha<br>1.0000 kg/ha |
| 8 | LOGRAN 20 WG<br>betaine | 0.0100 kg/ha<br>2.0000 kg/ha |
| 9 | RATIO<br>SITO+ | 0.0070 kg/ha<br>0.1000 l/ha |
| 10 | RATIO 50 T<br>SITO+ | 0.0105 kg/ha<br>0.1000 l/ha |
| 11 | RATIO<br>SITO+<br>betaine | 0.0070 kg/ha<br>0.1000 l/ha<br>1.0000 kg/ha |
| 12 | LOGRAN 20 WG<br>CADENCE 70 WG<br>SITO+ | 0.0200 kg/ha<br>0.0500 kg/ha<br>0.2000 l/ha |
| 13 | LOGRAN 20 WG<br>CADENCE 70 WG<br>SITO+ | 0.0100 kg/ha<br>0.0250 kg/ha<br>0.2000 l/ha |

The tests were performed as field tests in two different locations: at Jokioinen (test 1) and Ylistaro (test 2). The cultivated plant was barley. The tests were performed in random order within blocks, the gross area of an experimental plot was 3×9 m, and the tests were replicated four times. In test 1, barley was sown on May 22, 1996, and the harvest was gathered on Sep. 3, 1996. The soil was heavy clay, and 315 kg/ha (N-P-K 26-2-3) of fertiliser was used. In test (2), barley was sown on May 14, 1996 and the harvest was gathered on Sep. 4, 1996. The soil was mud, and 500 kg/ha (N-P-K 20-2-12) of fertiliser was used. In the period of growth of 1996, May, June and July were rainier and cooler than on the average. About half of the days in both May and June were rainy days. The sprayings were performed in both tests on Jun. 17, 1996; within a week after the spraying both test sites had about 40 mm of rainfall. The rainfall in July was almost double the long-term average. August, on the other hand, was drier and warmer than on the average. In spite of the bad weather, the harvest obtained in the tests was good: 4200 to 5500 kg/ha.

The number of weeds was counted and the dry weight was weighed five weeks after the spraying. The proportion of weeds is also stated as a ratio to the number of weeds (=100) in the untreated treatment.

Figure 1B:
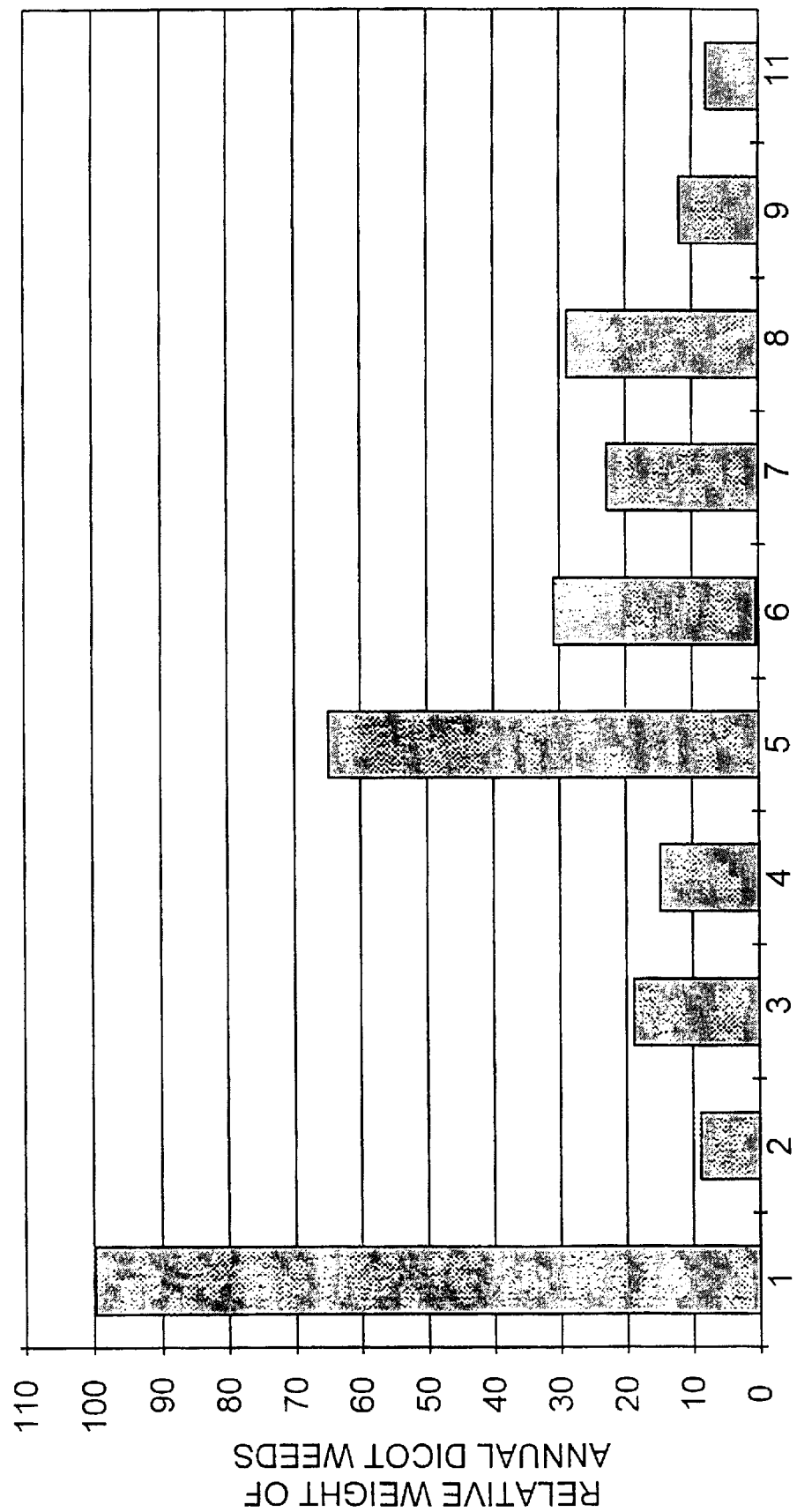
FIG. 1B is a graph showing the summary of results of Example 2 illustrating the effect of betaine and herbicide treatment on the relative weight of dicot weeds.
Figure 2A:
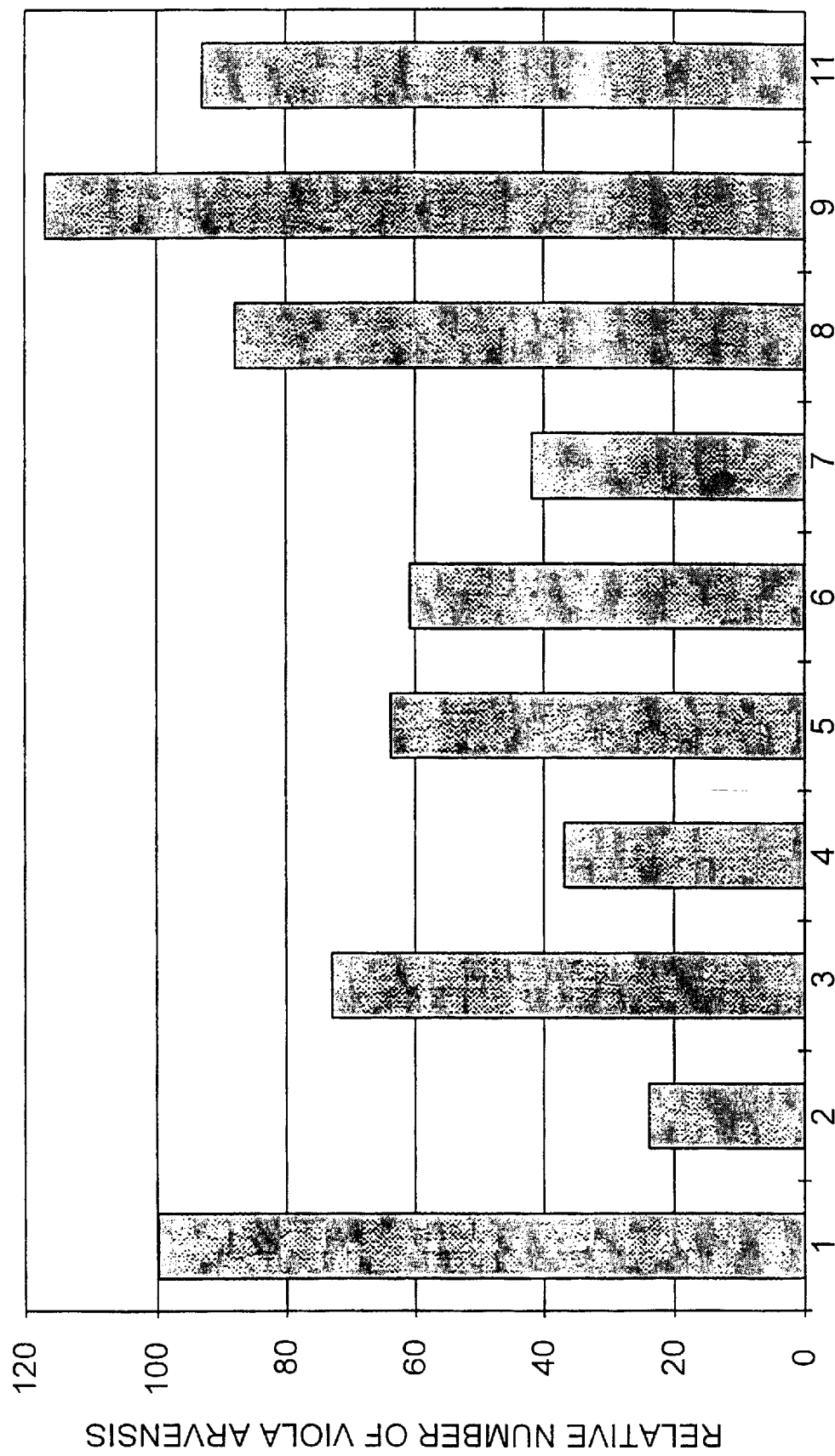
FIG. 2A is a graph showing the summary of results of Example 2 illustrating the effect of betaine and herbicide treatment on the relative number of *viola arvensis;*
Figure 2B:
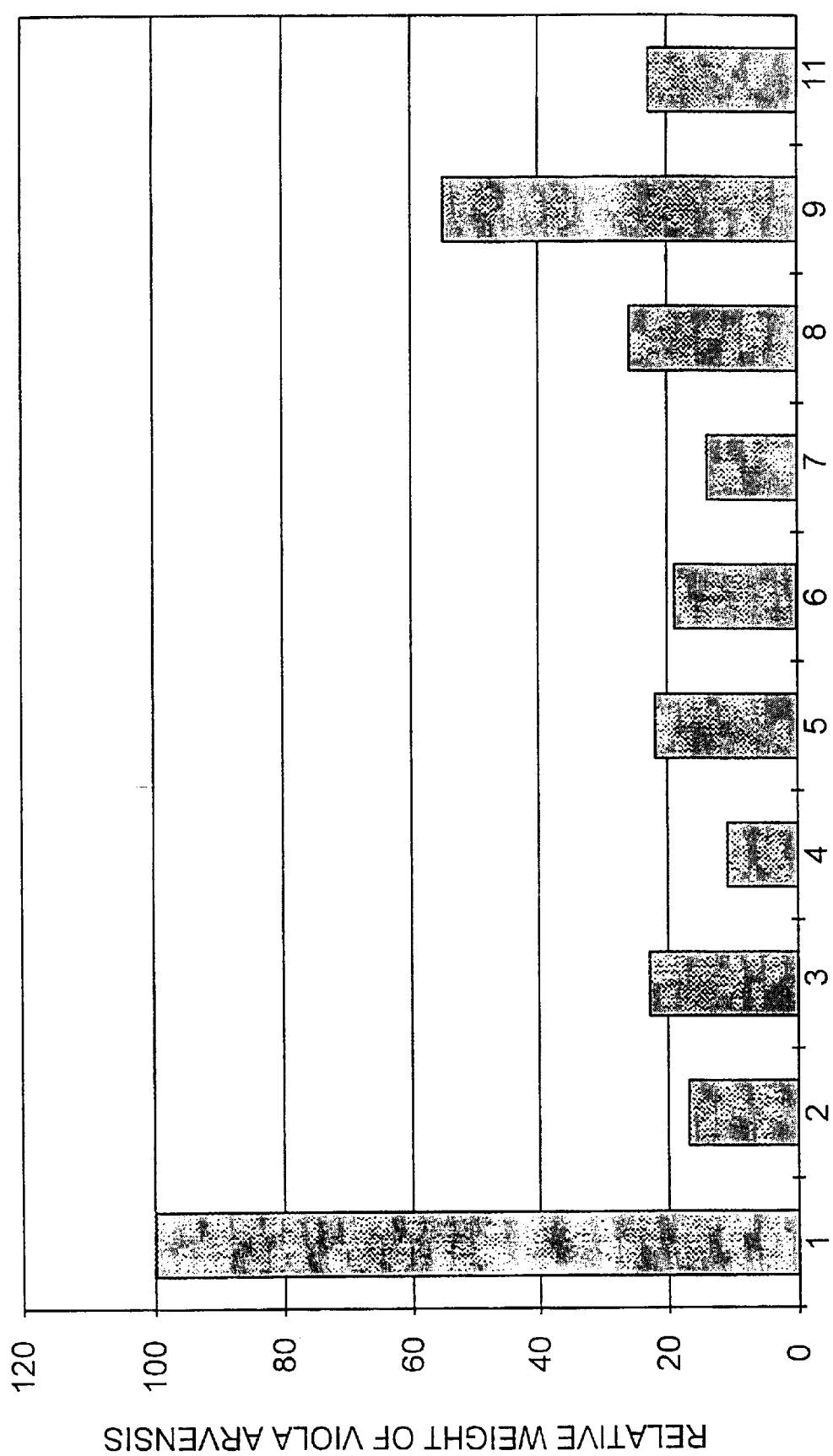
FIG. 2B is a graph showing the summary of results of Example 2 illustrating the effect of betaine and herbicide treatment on the relative weight of *viola arvensis;*
Figure 3A:
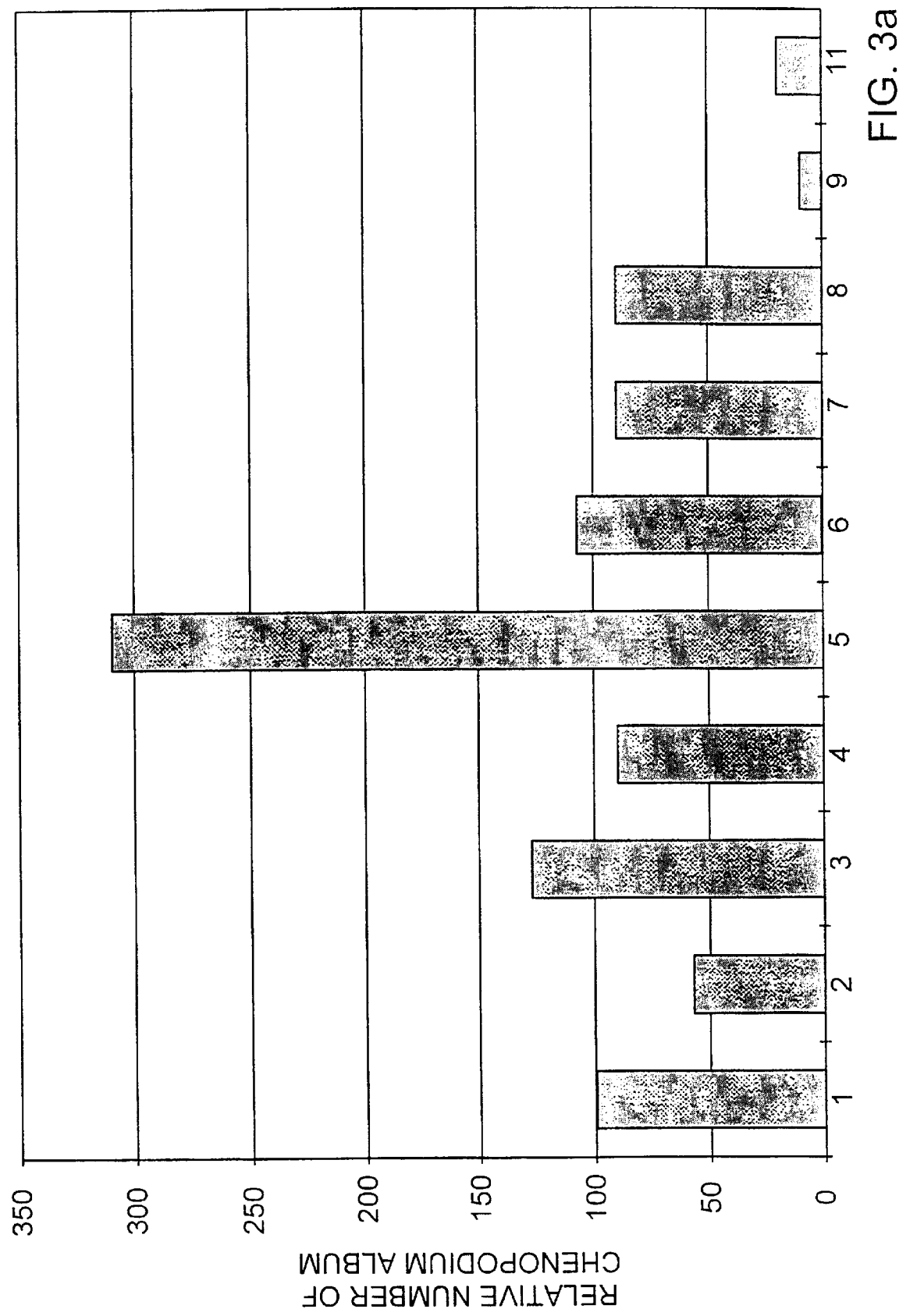
FIG. 3A is a graph showing the summary of results of Example 2 illustrating the effect of betaine and herbicide treatment on the relative number of *chenopodium album;*
Figure 3B:
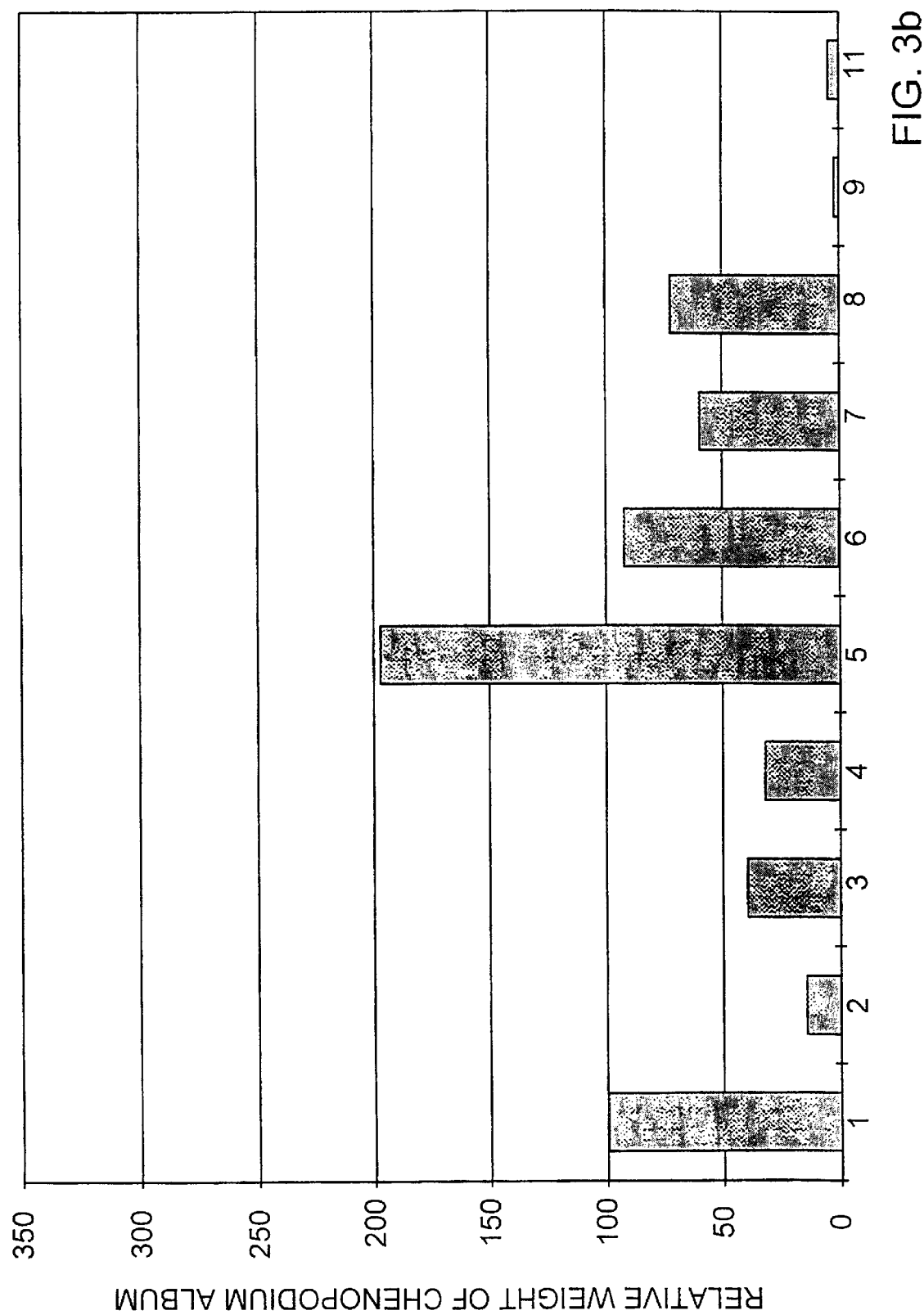
FIG. 3B is a graph showing the summary of results of Example 2 illustrating the effect of betaine and herbicide treatment on the relative weight of *chenopodium album;*

The number of dicotyledonous weeds in test 1 was 279 per m², and their dry weight was 27.5 g/m². There were over 40 goosefoots, forget-me-nots, hemp nettles and violets per m². In addition, there were 28 to 35 common chickweeds, black bindweeds and nippleworts per m². The proportion of hemp nettle and goosefoot in the total amount of weeds was 62%. In test 2 the number of weeds was smaller, 104 per m², and their dry weight was 10.0 g/m². The proportion of three species of weeds, i.e. goosefoot, violet and scentless mayweed, was about 70% in the total number of weeds. The results of tests 1 and 2 are shown in Tables 6a to 6c, and 7a and 7b, respectively. A summary of the results obtained in the tests is presented graphically in FIGS. 1 to 3, in which FIGS. 1a and 1b illustrate the effect of betaine and herbicide treatments on the relative number and weight of dicotyledonous weeds, respectively, and FIGS. 2a and 2b, and 3a and 3b show the effect of the treatments on the relative number and weight of two dominant species, i.e. violet and goosefoot.

TABLE 6a

The number of dicotyledonous weeds (per m² and given with relative numbers) after treatment

| Species | | Treatment number | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Hemp nettle | per m² | 41 | 9 | 12 | 15 | 10 | 15 | 14 | 30 | 21 | 24 | 18 | 6 | 27 |
| | rel. | 100 | 21 | 30 | 37 | 25 | 36 | 33 | 73 | 52 | 59 | 44 | 15 | 67 |
| Goosefoots | | 47 | 32 | 70 | 45 | 170 | 55 | 43 | 42 | 4 | 3 | 9 | 27 | 102 |
| | | 100 | 68 | 148 | 96 | 361 | 116 | 90 | 88 | 9 | 6 | 18 | 56 | 216 |
| Nipplewort | | 28 | 12 | 19 | 23 | 15 | 11 | 8 | 13 | 15 | 22 | 22 | 18 | 24 |
| | | 100 | 41 | 68 | 80 | 54 | 39 | 29 | 45 | 54 | 79 | 79 | 64 | 86 |
| Common chickweed | | 35 | 2 | 5 | 8 | 3 | 4 | 1 | 6 | 5 | 5 | 3 | 4 | 8 |
| | | 100 | 6 | 13 | 22 | 9 | 10 | 3 | 16 | 15 | 15 | 7 | 12 | 23 |
| Forget-me-nots | | 43 | 12 | 2 | 19 | 12 | 18 | 10 | 30 | 30 | 15 | 18 | 4 | 14 |
| | | 100 | 27 | 5 | 44 | 28 | 41 | 22 | 69 | 71 | 34 | 41 | 8 | 32 |
| Field pansy | | 43 | 13 | 22 | 17 | 22 | 28 | 16 | 40 | 53 | 53 | 45 | 23 | 77 |
| | | 100 | 29 | 50 | 38 | 50 | 64 | 36 | 93 | 123 | 123 | 105 | 54 | 179 |
| Black bindweed | | 31 | 6 | 3 | 5 | 2 | 1 | 2 | 3 | 20 | 13 | 0 | 2 | 13 |
| | | 100 | 18 | 10 | 15 | 7 | 3 | 7 | 8 | 65 | 42 | 0 | 7 | 42 |
| Total of other dicotyledonous weeds | | 12 | 6 | 11 | 8 | 5 | 8 | 4 | 3 | 11 | 6 | 10 | 5 | 7 |
| | | 100 | 46 | 88 | 67 | 42 | 63 | 29 | 25 | 92 | 46 | 79 | 38 | 58 |
| Total of all dicotyledonous weeds | | 279 | 89 | 142 | 138 | 238 | 137 | 96 | 164 | 159 | 140 | 123 | 88 | 271 |
| | | 100 | 32 | 51 | 49 | 86 | 49 | 34 | 59 | 57 | 50 | 44 | 31 | 97 |

TABLE 6b

Dry weight of dicotyledonous weeds (per m² and given with relative numbers) after treatment

| Species | | Treatment number | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Hemp nettle | per m² | 9.2 | 0.1 | 0.3 | 0.3 | 0.3 | 0.4 | 0.4 | 0.6 | 0.7 | 0.6 | 0.7 | 0.1 | 0.7 |
| | rel. | 100 | 1 | 3 | 3 | 3 | 4 | 4 | 7 | 8 | 6 | 8 | 1 | 7 |
| Goosefoots | | 7.8 | 1.2 | 4.3 | 2.1 | 19.6 | 8.0 | 5.9 | 6.3 | 0.1 | 0.1 | 0.2 | 0.7 | 3.1 |
| | | 100 | 15 | 55 | 26 | 251 | 103 | 75 | 80 | 1 | 1 | 2 | 9 | 39 |
| Nipplewort | | 2.1 | 0.3 | 0.3 | 0.4 | 0.3 | 0.2 | 0.2 | 0.4 | 0.6 | 0.5 | 0.3 | 0.3 | 0.6 |
| | | 100 | 12 | 15 | 17 | 15 | 10 | 7 | 15 | 20 | 29 | 24 | 12 | 27 |
| Common chickweed | | 1.8 | 0.0 | 0.1 | 0.0 | 0.0 | 0.0 | 0.0 | 0.1 | 0.0 | 0.1 | 0.0 | 0.0 | 0.1 |
| | | 100 | 0 | 6 | 0 | 0 | 0 | 0 | 3 | 0 | 3 | 0 | 0 | 6 |
| Forget-me-nots | | 1.0 | 0.1 | 0.1 | 0.2 | 0.2 | 0.3 | 0.1 | 0.4 | 0.4 | 0.2 | 0.2 | 0.1 | 0.2 |
| | | 100 | 10 | 5 | 15 | 15 | 25 | 10 | 35 | 35 | 15 | 20 | 5 | 20 |
| Field pansy | | 1.5 | 0.1 | 0.3 | 0.1 | 0.3 | 0.3 | 0.1 | 0.3 | 0.9 | 0.6 | 0.4 | 0.2 | 0.8 |
| | | 100 | 7 | 17 | 3 | 17 | 17 | 7 | 17 | 59 | 41 | 24 | 14 | 52 |
| Black bindweed | | 3.3 | 0.2 | 0.1 | 0.1 | 0.1 | 0.0 | 0.0 | 0.0 | 0.5 | 0.3 | 0.0 | 0.1 | 0.4 |
| | | 100 | 5 | 3 | 3 | 2 | 0 | 0 | 0 | 15 | 9 | 0 | 2 | 12 |
| Total of other dicotyledonous weeds | | 1.2 | 0.2 | 0.3 | 0.2 | 0.5 | 0.5 | 0.2 | 0.1 | 0.2 | 0.1 | 0.1 | 0.2 | 0.1 |
| | | 100 | 13 | 21 | 13 | 42 | 42 | 13 | 4 | 13 | 4 | 4 | 13 | 4 |
| Total of all dicotyledonous weeds | | 27.5 | 2.0 | 6.0 | 3.5 | 21.0 | 9.5 | 6.5 | 8.0 | 3.5 | 2.5 | 2.5 | 2.0 | 5.5 |
| | | 100 | 7 | 22 | 13 | 76 | 35 | 24 | 29 | 13 | 9 | 9 | 7 | 20 |

TABLE 6c

Effect of betaine treatment on phytotoxicity of herbicides

| Phytotoxicity 0–100 | Treatment number | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| | 0 | 3 | 2 | 1 | 0 | 0 | 0 | 1 | 2 | 2 | 0 | 6 | 3 |

TABLE 7a

| Species | | Treatment number | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Goosefoots | per $m^2$ | 11 | 2 | 5 | 6 | 9 | 8 | 8 | 8 | 1 | 1 | 2 | 1 | 2 |
| | rel. | 100 | 18 | 45 | 55 | 82 | 73 | 73 | 73 | 9 | 9 | 18 | 9 | 18 |
| Field pansy | | 22 | 3 | 25 | 7 | 20 | 12 | 12 | 17 | 23 | 16 | 14 | 9 | 11 |
| | | 100 | 14 | 114 | 32 | 91 | 55 | 55 | 77 | 105 | 73 | 64 | 41 | 50 |
| Scentless mayweed | | 37 | 0 | 5 | 0 | 1 | 0 | 2 | 1 | 2 | 2 | 4 | 2 | 2 |
| | | 100 | 0 | 14 | 0 | 3 | 0 | 5 | 3 | 5 | 5 | 11 | 5 | 5 |
| Common chickweed | | 13 | 0 | 1 | 0 | 0 | 1 | 0 | 0 | 0 | 0 | 0 | 0 | 0 |
| | | 100 | 0 | 8 | 0 | 0 | 8 | 0 | 0 | 0 | 0 | 0 | 0 | 0 |
| Forget-me-nots | | 6 | 0 | 4 | 2 | 4 | 2 | 2 | 3 | 2 | 2 | 8 | 0 | 2 |
| | | 100 | 0 | 67 | 33 | 67 | 33 | 33 | 50 | 33 | 33 | 133 | 0 | 33 |
| Black bindweed | | 5 | 0 | 1 | 1 | 2 | 0 | 2 | 0 | 0 | 3 | 1 | 0 | 1 |
| | | 100 | 0 | 20 | 20 | 40 | 0 | 40 | 0 | 0 | 60 | 20 | 0 | 20 |
| Total of other | | 10 | 1 | 5 | 5 | 6 | 3 | 6 | 6 | 1 | 1 | 5 | 2 | 3 |
| dicotyledonous weeds | | 100 | 10 | 50 | 50 | 60 | 30 | 60 | 60 | 10 | 10 | 50 | 20 | 30 |
| Total of all dicotyledonous | | 104 | 6 | 46 | 22 | 43 | 26 | 32 | 35 | 29 | 26 | 34 | 14 | 21 |
| weeds | | 100 | 6 | 44 | 21 | 41 | 25 | 31 | 34 | 28 | 25 | 33 | 13 | 20 |

TABLE 7b

| Species | | Treatment number | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Goosefoot | per $m^2$ | 3.3 | 0.8 | 0.2 | 1.8 | 2.4 | 1.5 | 1.2 | 1.9 | 0.0 | 0.0 | 0.1 | 0.1 | 0.1 |
| | rel. | 100 | 24 | 6 | 55 | 73 | 45 | 36 | 48 | 0 | 0 | 3 | 3 | 3 |
| Field pansy | | 1.0 | 0.3 | 0.3 | 0.2 | 0.3 | 0.2 | 0.2 | 0.4 | 0.5 | 0.3 | 0.2 | 0.2 | 0.3 |
| | | 100 | 30 | 30 | 20 | 30 | 20 | 20 | 40 | 50 | 30 | 20 | 20 | 30 |
| Scentless mayweed | | 2.7 | 0.0 | 0.1 | 0.0 | 0.1 | 0.0 | 0.0 | 0.1 | 0.2 | 0.1 | 0.1 | 0.2 | 0.1 |
| | | 100 | 0 | 4 | 0 | 4 | 0 | 0 | 4 | 7 | 4 | 4 | 7 | 4 |
| Common chickweed | | 0.9 | 0.0 | 0.1 | 0.0 | 0.0 | 0.1 | 0.0 | 0.0 | 0.0 | 0.0 | 0.0 | 0.0 | 0.0 |
| | | 100 | 0 | 11 | 0 | 0 | 11 | 0 | 0 | 0 | 0 | 0 | 0 | 0 |
| Forget-me-nots | | 0.4 | 0.1 | 0.1 | 0.1 | 0.2 | 0.2 | 0.1 | 0.1 | 0.2 | 0.2 | 0.1 | 0.0 | 0.1 |
| | | 100 | 25 | 25 | 25 | 50 | 50 | 2 5 | 25 | 50 | 50 | 25 | 0 | 25 |
| Black bindweed | | 0.3 | 0.0 | 0.1 | 0.0 | 0.1 | 0.0 | 0.1 | 0.0 | 0.0 | 0.1 | 0.1 | 09.0 | 0.1 |
| | | 100 | 0 | 33 | 0 | 33 | 0 | 33 | 0 | 0 | 33 | 33 | 0 | 33 |
| Total of other | | 1.4 | 0.1 | 0.3 | 0.4 | 0.5 | 0.2 | 0.8 | 0.6 | 0.1 | 0.1 | 0.2 | 0.1 | 0.2 |
| dicotyledonous weeds | | 100 | 7 | 21 | 28 | 35 | 14 | 57 | 42 | 7 | 7 | 14 | 7 | 14 |
| Total of all dicotyledonous | | 10.0 | 1.3 | 1.2 | 2.5 | 3.5 | 2.2 | 2.4 | 3.1 | 1.0 | 0.8 | 0.7 | 0.7 | 1.0 |
| weeds | | 100 | 13 | 12 | 25 | 35 | 22 | 24 | 31 | 10 | 8 | 7 | 7 | 10 |

The results show that betaine improved the effect of herbicide on the number of weeds by about 7% and on the dry weight by about 3%. Particularly in a triple mixture comprising herbicide (Logran or Ratio), adhesive agent (Sito+), and 1.0 kg/ha of betaine, betaine improved the effect of the herbicide on violet, goosefoot, forget-me-not, and black bindweed. The most significant result was that betaine notably reduced the phytotoxicity of the herbicide preparations.

EXAMPLE 3

The test described in example 2 was repeated using the same herbicides, Logran 20 WG, Ciba-Geigy, and Ratio, Du Pont. The difference from the experiment of example 2 was that the cultivated plant was oat (Yty).

The test was performed as a field test at Jokioinen (test 3) in the same period of growth and in the same way as described in example 2. Oat was sown on May 23, 1996, and the harvest was gathered on Sep. 11, 1996. The soil was heavy clay, and 320 kg/ha (N-P-K 26-2-3) of fertiliser was used. The oat comprised a large number of weeds (over 500 per $m^2$); heavy rainfall delayed the sprayings, which were conducted late, i.e. on Jun. 28, 1996, by which time oat straw had already started to grow. The treatments are shown in Table 8.

TABLE 8

Treatments of oat

| Treatment number | Material applied | Dose |
| --- | --- | --- |
| 1 | untreated | — — |
| 2 | LOGRAN 20 WG | 0.0100 kg/ha |
|   | SITO+ | 0.2000 l/ha |
| 3 | LOGRAN 20 WG | 0.0100 kg/ha |
|   | SITO+ | 0.2000 l/ha |
|   | Betaine | 1.0000 kg/ha |
| 4 | LOGRAN 20 WG | 0.0100 kg/ha |
|   | Betaine | 0.1000 kg/ha |
| 5 | LOGRAN 20 WG | 0.0100 kg/ha |
|   | Betaine | 0.5000 kg/ha |
| 6 | LOGRAN 20 WG | 0.0100 kg/ha |
|   | Betaine | 1.0000 kg/ha |
| 7 | LOGRAN 20 WG | 0.0100 kg/ha |
|   | Betaine | 2.0000 kg/ha |

Figure 4:
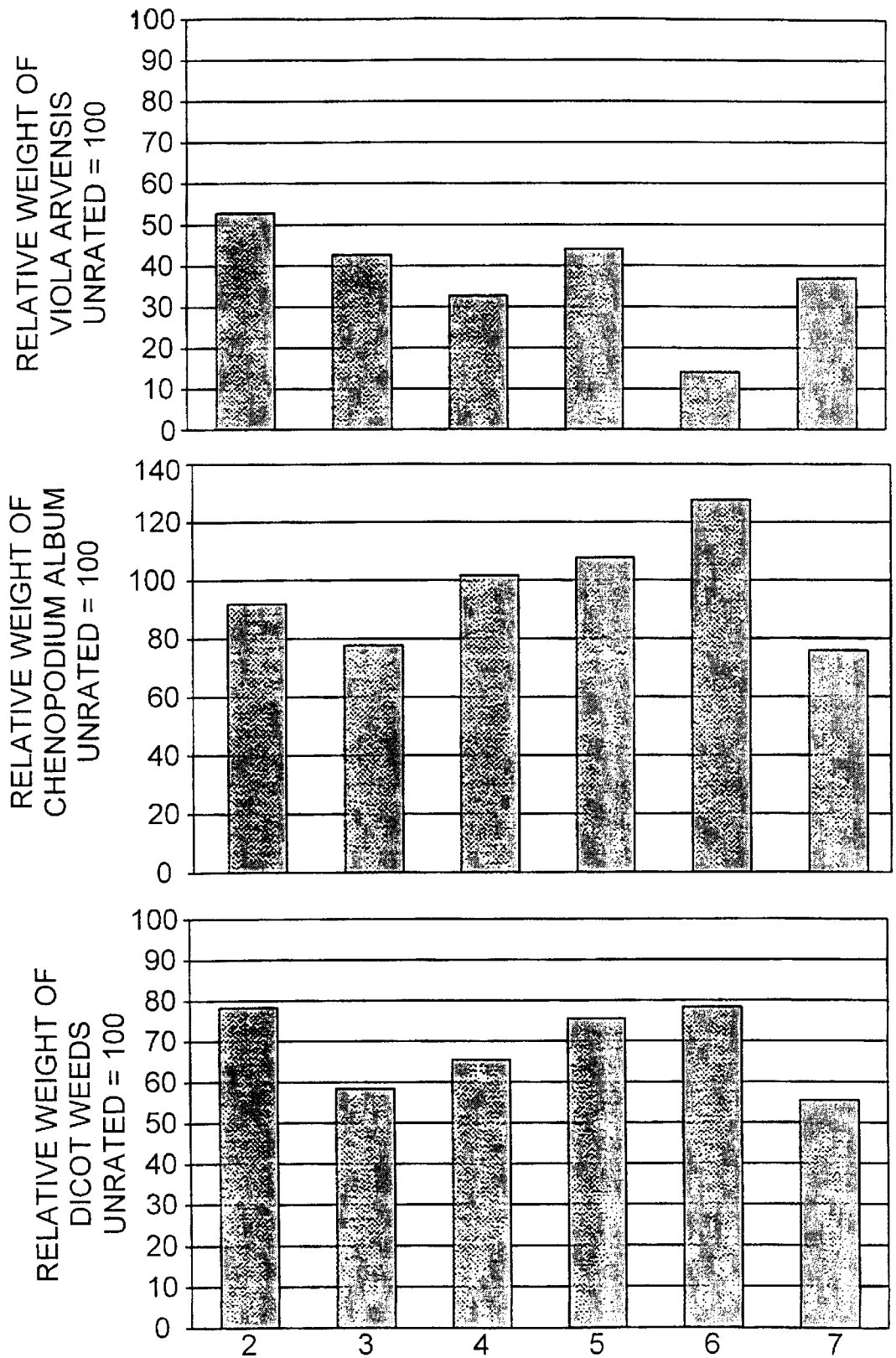
FIG. 4A is a graph showing the effects of betaine additions in improving the effects of herbicide on dicot weeds.
FIG. 4B is a graph showing the effects of betaine additions in improving the effects of herbicide on *chenopodium album.
* and FIG. 4C is a graph showing the effects of betaine additions in improving the effects of herbicide on *viola arvensis.*

Of the total amount of weeds, 51% were goosefoot and 31% violet. The results show that the effect of betaine was significant: a betaine addition of 1.0 kg/ha to a standard spraying mixture improved the effect of the herbicide on the two dominant species by 11 to 14%, and the total effect by 20%. A betaine dose of 2.0 kg/ha improved the total effect on weeds by up to 24%. In this test, the greatest betaine dose of 2.0 kg/ha gave the best results in respect of both weed control and oat yield. The effects on the dry weight of weeds (Aug. 22, 1996) are shown in numbers in Table 9 and graphically in FIG. 4.

TABLE 9

Weight of dicotyledonous weeds (g per m$^2$ and given with relative numbers) after treatment

| Species | | Treatment number | | | | | | |
| --- | --- | --- | --- | --- | --- | --- | --- | --- |
|  |  | 1 | 2 | 3 | 4 | 5 | 6 | 7 |
| Goosefoot | dry weight per m$^2$ | 8.7 | 8.1 | 6.9 | 9.0 | 9.4 | 11.2 | 6.7 |
|  | rel. | 100 | 93 | 79 | 103 | 108 | 128 | 77 |
| Field pansy |  | 5.3 | 2.9 | 2.3 | 1.8 | 2.4 | 0.8 | 2.0 |
|  |  | 100 | 54 | 43 | 33 | 45 | 15 | 37 |
| Common chickweed |  | 0.4 | 1.8 | 0.2 | 0.1 | 0.2 | 0.9 | 0.2 |
|  |  | 100 | 514 | 43 | 14 | 57 | 243 | 43 |
| Bedstaws |  | 0.6 | 0.1 | 0.1 | 0.1 | 0.4 | 0.3 | 0.0 |
|  |  | 100 | 8 | 8 | 17 | 58 | 42 | 0 |
| Dead nettles |  | 0.1 | 0.3 | 0.1 | 0.2 | 0.1 | 0.0 | 0.0 |
|  |  | 100 | 300 | 50 | 200 | 50 | 0 | 0 |
| Total of other dicotyledonous weeds |  | 1.9 | 0.3 | 0.6 | 0.1 | 0.4 | 0.3 | 0.3 |
|  |  | 100 | 16 | 32 | 5 | 18 | 13 | 16 |
| Total of all dicotyledonous weeds |  | 17.0 | 13.4 | 10.1 | 11.2 | 12.7 | 13.3 | 9.3 |
|  |  | 100 | 79 | 59 | 66 | 75 | 78 | 55 |

What is claimed is:

1. A method of improving the effect of herbicides on plants comprising applying to the plant and/or soil surrounding it a herbicide and glycine betaine.

2. The method of claim 1 wherein the glycine betaine and herbicide are applied to plant leafs.

3. The method of claim 1 wherein the glycine betaine and herbicide are applied to soil surrounding plants.

4. The method of claim 1 wherein the amount of glycine betaine applied is about 0.01 to 10 kg/ha.

5. The method of claim 1 wherein the amount of glycine betaine applied is about 0.1 to 6 kg/ha.

6. The method of claim 1 wherein the amount of glycine betaine applied is about 2 to 4 kg/ha.

7. The method of claim 1 wherein the amount of glycine betaine applied is about 1 to 2 kg/ha.

8. The method of claim 1 wherein the glycine betaine and herbicide are applied multiple times during plant growth.

9. The method of claim 1 wherein the glycine betaine and herbicide are applied together with a pesticide, fertilizer or surfactant.

10. The method of claim 1 wherein the glycine betaine and herbicide are applied as an aqueous solution.

11. The method of claim 1 wherein the glycine betaine and herbicide are applied as an emulsion, suspension or as granules.

12. The method of claim 1 wherein the herbicide is a triazine or a sulphonylurea compound.

13. A method of enchancing the effect of a herbicide on weeds comprising applying to weeds a herbicide together with glycine betaine in an amount to enhance the effect of the herbicide.

14. A method of killing weeds by enhancing the effect of a herbicide on weeds while reducing herbicide phytotoxicity to crop plants comprising applying to an area containing both weeds and crop plants a herbicide together with glycine betaine in an amount sufficient to enhance the effect of the herbicide on weeds while reducing herbicide phytotoxicity to crop plants.

15. A herbicidal composition comprising a herbicide together with a herbicide-enhancing amount of glycine betaine and optionally a herbicidal adjuvant or additive.

16. The composition of claim 15 in the form of an emulsion, suspension or granules.

17. The composition of claim 15 in the form of an aqueous solution or solution in an organic solvent.

18. The composition of claim 15 in the form of a solid.

19. The composition of claim 15 wherein the herbicide is a triazine or a sulphonylurea compound.

* * * * *